United States Patent
Jonsen et al.

(10) Patent No.: US 9,403,026 B2
(45) Date of Patent: *Aug. 2, 2016

(54) LANGUAGE PLACARD FOR AN AUTOMATED EXTERNAL DEFIBRILLATOR

(71) Applicant: KONINKLIJKE PHILIPS N.V., Eindhoven (NL)

(72) Inventors: Eric Jonsen, Seattle, WA (US); Jacco Christof Eerden, Eindhoven (NL); Daniel J. Powers, Issaquah, WA (US); Kurt Vincent Fischer, Edmonds, WA (US); Christian James Richard, Shoreline, WA (US); Alan Paul Greenstein, Seattle, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 64 days.

This patent is subject to a terminal disclaimer.

(21) Appl. No.: 14/376,046

(22) PCT Filed: Jan. 25, 2013

(86) PCT No.: PCT/IB2013/050651
§ 371 (c)(1),
(2) Date: Jul. 31, 2014

(87) PCT Pub. No.: WO2013/114256
PCT Pub. Date: Aug. 8, 2013

(65) Prior Publication Data
US 2015/0005836 A1    Jan. 1, 2015

Related U.S. Application Data

(60) Provisional application No. 61/593,965, filed on Feb. 2, 2012.

(51) Int. Cl.
| | | |
|---|---|---|
| A61N 1/39 | (2006.01) |
| G06F 17/20 | (2006.01) |
| G06F 17/27 | (2006.01) |
| G06F 17/28 | (2006.01) |
| G06F 9/44 | (2006.01) |
| A61N 1/372 | (2006.01) |

(52) U.S. Cl.
CPC .......... *A61N 1/3993* (2013.01); *A61N 1/37247* (2013.01); *G06F 9/4448* (2013.01); *G06F 17/289* (2013.01)

(58) Field of Classification Search
CPC ... A61N 1/36014; A61N 1/3625; A61N 1/39; A61N 1/3993; G06F 9/4448; G06F 17/28; G06F 17/289
USPC ........................................... 704/8; 607/2, 4–6
See application file for complete search history.

(56) References Cited

U.S. PATENT DOCUMENTS

| | | |
|---|---|---|
| 6,154,673 A | 11/2000 | Morgan |
| 7,653,435 B2 | 1/2010 | Halsne |
| 2006/0178865 A1 | 8/2006 | Edwards |

FOREIGN PATENT DOCUMENTS

| | | |
|---|---|---|
| CN | 101001667 A | 7/2007 |
| WO | 9924114 A1 | 5/1999 |
| WO | 2008059397 A1 | 5/2008 |

*Primary Examiner* — Allen Porter, Jr.

(57) ABSTRACT

An automated external defibrillator (AED) 10 has a changeable language placard (20) which enables the AED to instruct the user in one or more languages. The placard includes a controlling element (120) which is sensed by the AED, and causes the AED to automatically switch the language mode into the corresponding placard language. The placard also includes visual guidance instructions (224, 226).

20 Claims, 5 Drawing Sheets

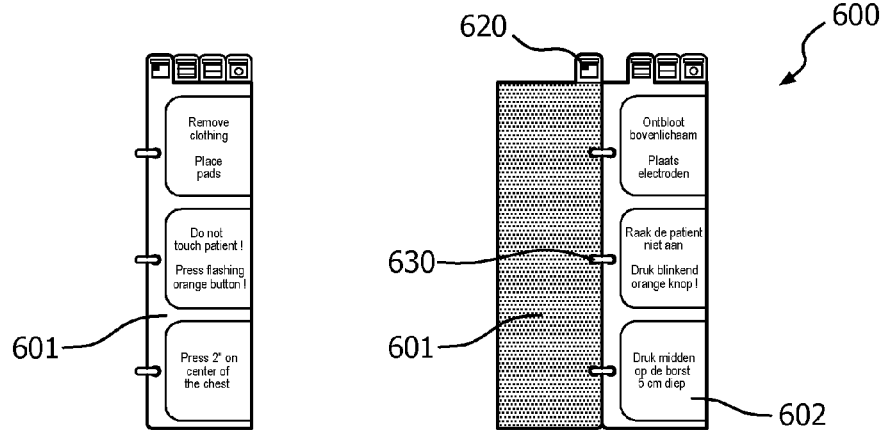
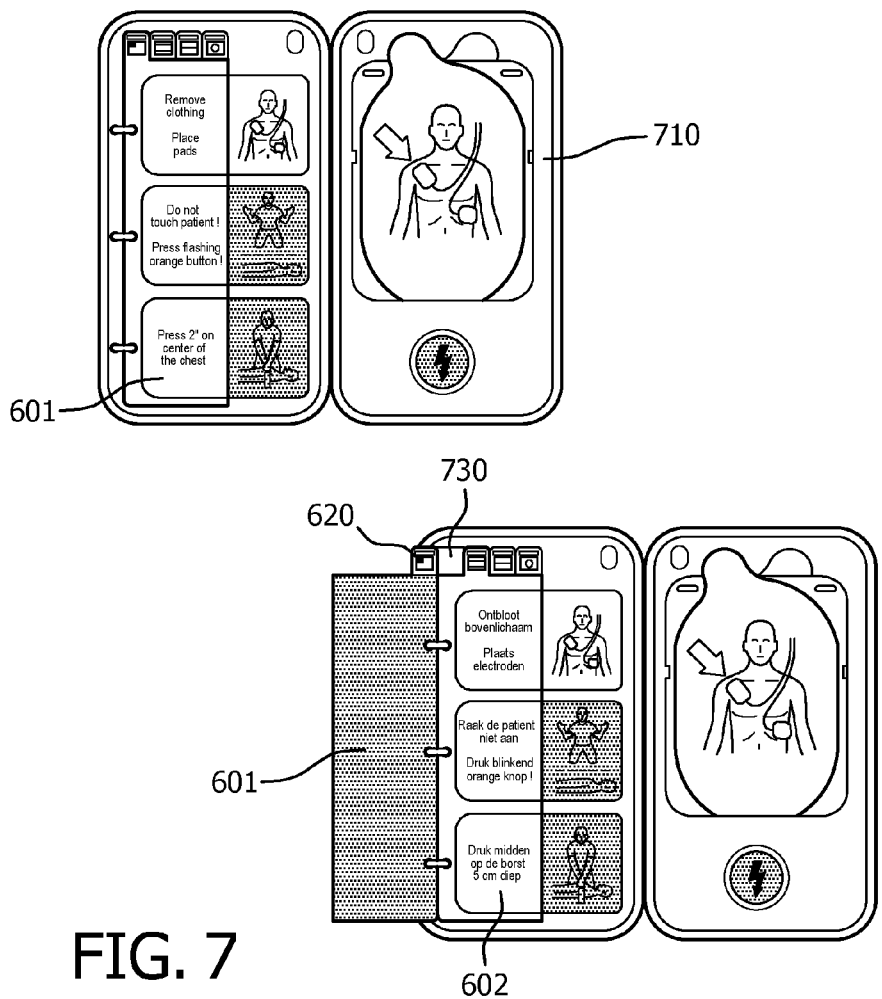
FIG. 7

LANGUAGE PLACARD FOR AN AUTOMATED EXTERNAL DEFIBRILLATOR

CROSS-REFERENCE TO PRIOR APPLICATIONS

This application is the U.S. National Phase application under 35 U.S.C. §371 of International Application No. PCT/IB2013/050651, filed on Jan. 25, 2013, which claims the benefit of U.S. Provisional Patent Application No. 61/593,965, filed on Feb. 2, 2012. These applications are hereby incorporated by reference herein.

This invention relates to an improved user interface for an automated external defibrillator (AED), and, in particular, to an AED which can be quickly configured to provide visual and aural instruction to the user in multiple languages. The invention also relates to a method for preparing the AED for operation in a desired language.

Sudden cardiac arrest ("SCA") most often occurs without warning, striking people with no history of heart problems. It is estimated that more than 1000 people per day are victims of sudden cardiac arrest in the United States alone. SCA results when the electrical component of the heart no longer functions properly, causing an abnormal sinus rhythm. One such abnormal sinus rhythm known as ventricular fibrillation ("VF") is caused by abnormal and very fast electrical activity in the heart. As a result, the heart fails to adequately pump blood through the body. VF may be treated by applying an electric shock to a patient's heart through the use of a defibrillator. Defibrillators include manual defibrillators, automatic or semi-automatic external defibrillators ("AEDs"), defibrillator/monitor combinations, advisory defibrillators and defibrillator trainers. The shock from the defibrillator clears the heart of abnormal electrical activity (in a process called "defibrillation") by producing a momentary asystole and an opportunity for the heart's natural pacemaker areas to restore normal rhythmic function. However, quick response after the onset of VF is critical because there is an increased likelihood that a patient will not be resuscitated or will suffer irreversible brain damage when the heart has not been pumping blood for more than 5 minutes.

Over the last several years defibrillators have become more portable and have begun moving into the hands of individuals who initially make contact with a person suffering from VF but have little or no formal medical training. As a result, equipment that was once available only in the hospital environment and operated by medically trained personnel is now being used in non-hospital environments by police officers, flight attendants and security guards, to name a few, as part of a first-line action in the administration of first aid. The benefit of making this equipment available is that it is more likely that a victim of SCA will receive the life-saving shock within the first few critical minutes of VF. Of course, with little or no medical training, the individuals who first make contact with a patient need to be instructed on the use of the defibrillator to deliver shock therapy. These defibrillators are often designed to operate nearly automatically and with little user intervention, often providing voice and text prompts to a medically untrained user on the operation of the defibrillator. Providing voice and text prompts for a user on the operation of a defibrillator reduces the amount of time necessary for the user to review protocols prior to deploying the defibrillator. Thus, a medically untrained individual first on the scene can nevertheless administer therapeutic shock to a patient in a short time.

As previously discussed, currently available external defibrillators often display instructions, status information or other information to assist the defibrillator operator on the operation of the defibrillator. Some external defibrillators announce such information audibly through a speaker, either in addition to displaying information or instead of displaying information. In areas where more than one language is commonly spoken, not necessarily with equal proficiency, there is a need to have a defibrillator that adapts the language of the prompts in response to the user's indication of language proficiency. This need is especially acute for defibrillators which are deployed in public areas, where there is no prior knowledge of which language a rescuer might speak. There are a number of locales where the need for a multilingual defibrillator is especially acute. The southern United States, for example, has a large number of people who speak exclusively English or exclusively Spanish. French Canada also has a population which may speak exclusively English or exclusively French. In Europe, many European languages coexist in a small area, increasing the likelihood of a rescuer who speaks a different language than the language set up on the defibrillator.

As a result, external defibrillators have been developed that can provide audible instructions and information on the operation of the defibrillator in different languages. These defibrillators are pre-programmed with audible instructions for more than one language from which audible instructions for one language are selected. Selection of the language in which the audible instructions and information are provided is typically made through button controls on the front panel of the defibrillator or through user responses to defibrillator prompts that are made during the operation of the defibrillator.

Although audible instructions on the operation of a defibrillator are available for different languages, the selection process for choosing which one of the languages to receive audible instructions can be distracting to a user, and also takes time to do. During a high stress rescue, any additional time or attention away from the task of applying rapid defibrillation to a patient only reduces the chance of success. Moreover, since the audible instructions are provided in only one language by the defibrillator, several rescuers having fluency in different languages will not be able to both benefit from the audible instructions provided by the defibrillator during administration of the therapy, thus precluding receipt of assistance from one or the other individual. Therefore, there is a need for a multilingual defibrillator providing audible instructions in more than one language during its operation.

In addition, the manufacture of AEDs must serve the needs of customers in a large number of countries. The current practice for manufacturing AEDs is to create a baseline AED using a default language stored in internal read-only memory. If a non-default language is needed by the customer, the baseline AED must be loaded with that language at the factory. No opportunity for changing languages in the field is possible. There is therefore a need for a more efficient method of providing a defibrillator which can be configured into different languages by, for example, the distributor or the end user.

The present invention is directed to a portable medical device, as exemplified by an AED, which can be configured by the user to provide operating instructions in one of several languages. The configuration is enabled by a language placard which can be removably installed on the AED and which provides visual instructions about using the AED during an emergency. The language placard also includes an encoded controlling element which uniquely identifies an audible language to be used by the AED. When the placard is joined to the AED, the AED senses the controlling element and automatically configures itself to provide audible instructions in the identified language.

It is thus one object of the present invention to provide a portable medical device which includes a memory having stored therein data files representative of audible prompts in a plurality of languages, a controller coupled to the memory and configured to operate the portable medical device in one of the languages, a sensing element for selecting one of the languages and a portable medical device case housing which includes the sensing element and a mount for a removable language placard. The invention further includes a language placard which can be mounted on the portable medical device mount and which comprises visual instructions for use. The placard also includes a controlling element which identifies the placard language and conveys the identification to the portable medical device via the sensing element. The features operate together to cause the portable medical device to immediately configure itself to generate user prompts in the identified language.

It is another object of the invention to provide a language placard for an AED. The language placard includes a panel or set of panels having written instructions in a first language, a controlling element to identify the language to an AED, and a securing element to mount the placard onto the AED.

It is a further object of the invention to provide a method for configuring the operating language of an AED during use. The method includes the steps of providing an AED and a language placard with written instructions in a particular language, mounting the placard onto the AED, sensing at the AED the placard language, and automatically operating the AED with user prompts in that language.

In the drawings:

FIGS. 6a and 6b are top views of a multi-panel language placard according to an embodiment of the present invention, showing the panel both closed and flipped open respectively.

FIG. 7 illustrates two views of an AED with a multi-panel language placard installed inside according to an alternative embodiment of the present invention, one view with the placard closed and another with the placard flipped open.

Figure 1:
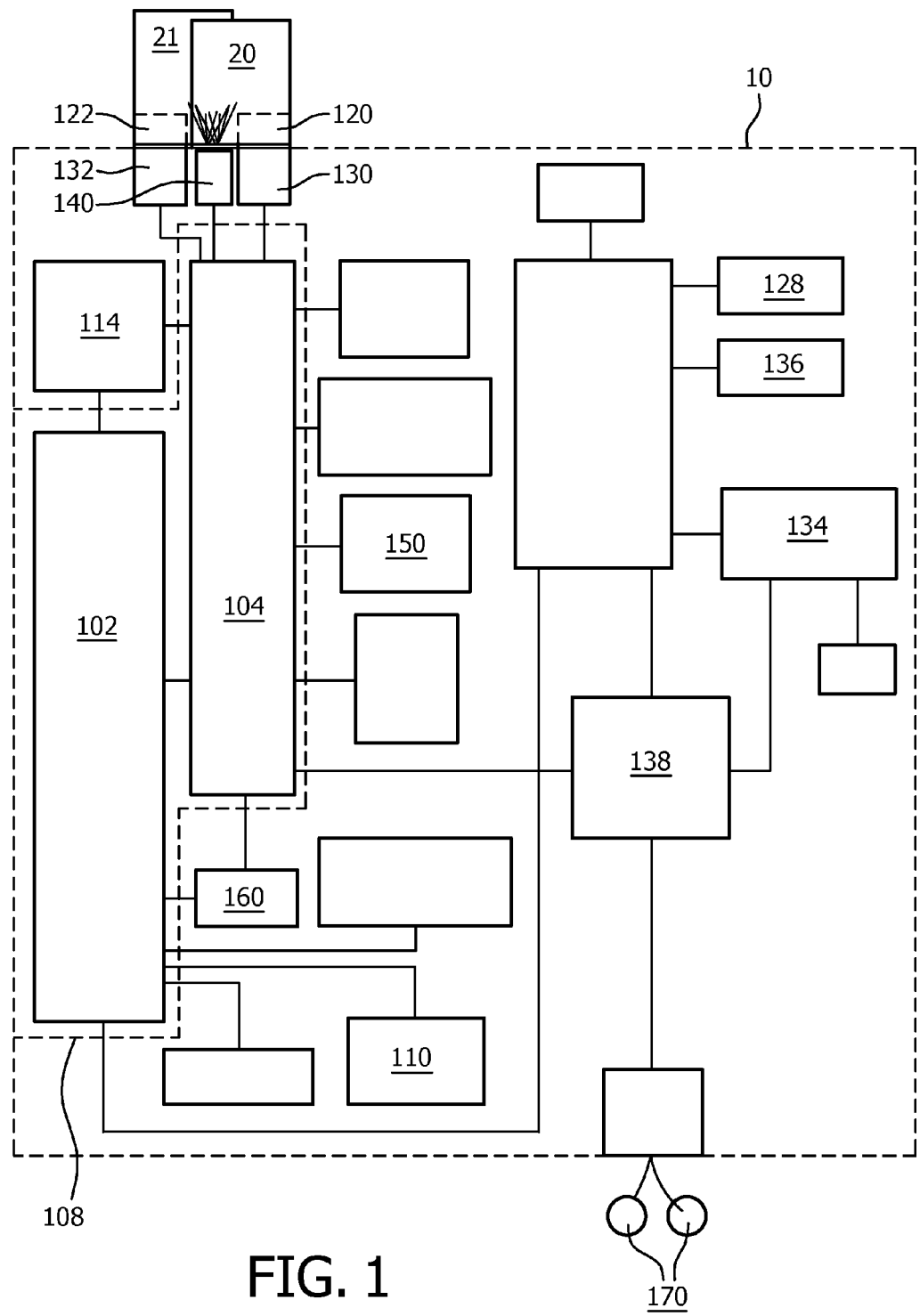
FIG. 1 is a functional block diagram of a defibrillator in which embodiments of the present invention can be implemented.

FIG. 1 is a block diagram of a multiple language portable medical device, in this example an AED 10, connected with a language placard 20 according to an embodiment of the present invention. FIG. 1 illustrates some conventional features of AED 10, including an energy source 138 which provides therapeutic voltage or current pulses to a pair of electrodes 170. Electrodes 170, disposed to be electrically attached to a patient (not shown), may also detect and monitor the patient's electrical heart rhythm for use in determining whether therapy is necessary. A battery 134 provides power to the AED 10. Status interface 128 provides a visual or aural indication of the readiness of the AED 10, such as with a blinking light, graphical indicator, or beeper.

The AED 10 is activated by the user, such as with on/off switch 136 or by sensing the opening of the AED housing with case opening sensor 110. A speaker 150 provides aural instructions, for example during a cardiac rescue, which guide the user through the appropriate steps of defibrillation and/or cardiopulmonary resuscitation. If a defibrillating shock is necessary, the user is guided to deliver the shock by pressing the shock button 160.

Control functions of the AED 10 may be divided among a main processing unit (MPU) 102 and a gate array 104. For example, MPU 102 may control the functions of the shock button 160, while gate array 304 controls speaker 150. Many variations of the controlling architecture within AED 10 are possible, and fall within the scope of the contemplated invention. All components which serve to manage the conventional functions of the AED 10 will be referred to as controller 108.

FIG. 1 also shows the features in AED 10 which enable use in a multiplicity of languages. Controller 108 accesses a read-only memory 114, which stores data relating to a plurality of languages. The appropriate language data may be used by controller 108 to generate audible prompts to the user via speaker 150. Controller 108 is preferably disposed to sense the progress of the procedure, and issue audible and/or visual prompts appropriate to that portion of the procedure.

Still referring to FIG. 1, language placard 20 is shown in connection with AED 10. As will be further described, language placard 20 includes user instructions printed in a first language. Language placard 20, mounted to the AED 10, thus provides visual guidance to the user. In alternate embodiments, a second language placard 21 having user instructions in a second language may be concurrently mounted on the AED 10 in a manner that only one placard is visible to the user at a time.

Each language placard 20, 21 includes an integrated controlling element, designated as element numbers 120 and 122 respectively. Each controlling element provides a unique signal which identifies the language contained on the placard. For example, if language placard 20 includes German instructions, controlling element 120 is encoded to identify the placard as German.

AED 10 further includes a sensing element 130 which is disposed to sense the controlling element 120 signal when the language placard 20 is mounted on AED 10. A second sensing element 132 may be disposed alongside sensing element 130 to sense controlling element 122 when the second language placard 21 is mounted on AED 10. When sensing element 130 senses the encoded identifier signal from controlling element 120, the signal is passed to controller 108. Controller 108 responds to the signal by accessing the corresponding language data from memory 114, and thereafter using that data to issue audible and verbal instructions to the user via speaker 150.

The particular means of communicating between controlling elements 120, 122 and corresponding sensing elements 130, 132 may be of any technology currently known in the art. In particular, the communication may be by active or passive optical sensing, by radio frequency identification, or through magnetic effects such as Hall Effect sensors. Communication may also be by direct electrical contact between pins on one element and encoded circuitry on the other element, or by mechanical key and sensing switch-type mechanisms.

FIG. 1 also illustrates an optional backlight 140, which may be disposed to illuminate the visible instructions on the language placard 20 or 21. Controller 108 may activate backlight 140 when the AED 10 is itself activated. Preferably, each language placard comprises several instructions, each pertaining to a step of the rescue procedure, and AED 10 comprises a separate backlight panel for each instruction. In the preferred embodiment, controller 108 sequentially illuminates each panel of backlight 140 according to a sensed step of the rescue procedure. Also in the preferred embodiment, each language placard has translucent areas through which the backlight 140 shines. The controller 108 further synchronizes the backlight 140 activation with the user prompts issued at speaker 150 in the desired language.

The portable medical device which interoperates with a language placard may be other than an AED 10. One example is a manual defibrillator. Another example is a defibrillator trainer that simulates the behavior of a manual or automatic/semi-automatic defibrillator in use, in which case the energy source 138 may be omitted. The invention may also be disposed on non-defibrillating portable medical devices, such as handheld diagnostic ultrasound machines, blood pressure monitors and the like.

Figure 2A:
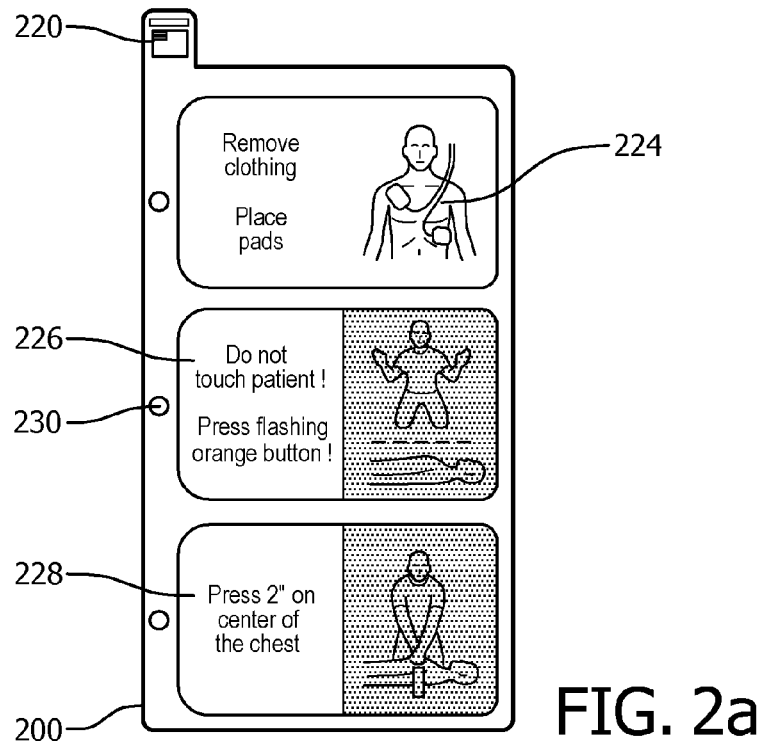
FIG. 2a is a top view of a full-panel language placard according to an embodiment of the present invention.

FIG. 2a is a top view of a full-panel language placard 200. According to this embodiment of the present invention, full-panel language placard 200 includes both a graphic instruction 224 set and a written instruction 226 set affixed or printed to the front of the placard 200. Preferably, each major stage of the underlying procedure is grouped into a separate instruction panel 228. In an even more preferred embodiment, each panel 228 is of a translucent material, such as a thin polymeric material, which allows the underlying backlight 170 on the AED to selectively illuminate and direct the user's attention to that particular stage. In the FIG. 2a illustration, the written instruction 226 set is in English, and includes each major step of a cardiac rescue.

Also affixed to the full-panel language placard 200 is a controlling element 220 of a technology as previously described. Controlling element 220 is preferably integrated into the placard 200 at a periphery of the placard such that it does not interfere with the visual instruction set 224, 226. Small indicia of language may be placed near the controlling element 220.

Figure 2B:
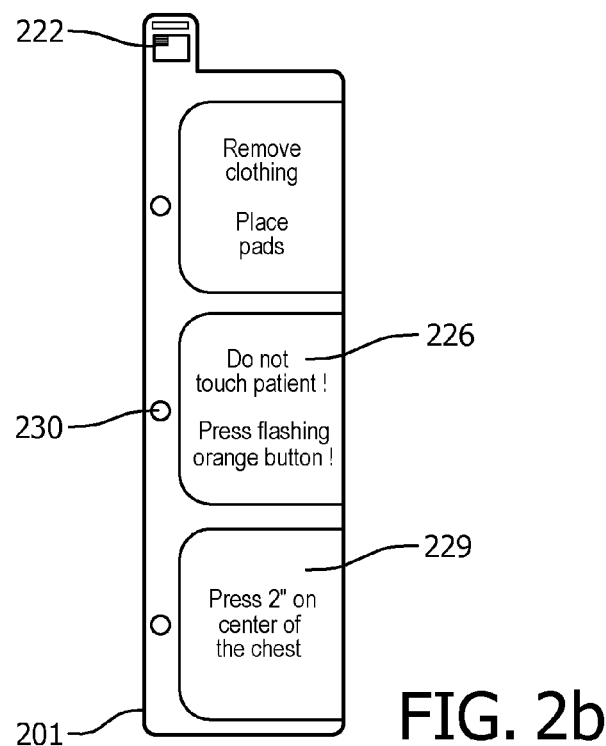
FIG. 2b is a top view of a half-panel language placard according to an embodiment of the present invention.

FIG. 2b is a top view of a half-panel language placard 201 according to another embodiment of the present invention. Half-panel placard 201 is constructed similarly to the full-panel language placard 200 except for lacking the portion which comprises a graphic instruction. According to this embodiment, half-panel language placard 201 includes only a written instruction 226 set affixed or printed to the front of the placard 201. Preferably, each major stage of the underlying procedure is grouped into a written instruction panel 229 similar to the left side of instruction panel 228. In an even more preferred embodiment, each panel 229 is of a translucent material, such as a thin polymeric material, which allows the underlying backlight 170 on the AED to selectively illuminate and direct the user's attention to that particular stage. In the FIG. 2b illustration, the written instruction 226 set is in English, and includes each major step of a cardiac rescue.

Affixed to the half-panel language placard 201 is a controlling element 222 of a technology as previously described. Controlling element 222 is preferably integrated into the placard 201 at a periphery of the placard such that it does not interfere with the visual instruction set 226. Small indicia of language may be placed near the controlling element 220.

The preferred material of construction for language placards 200, 201 is a durable and relatively stiff polymeric or plastic material. The material could also consist of a heavy stock paper coated with a printable polymeric material. The placards 200, 201 could also be constructed of two sheets with controlling element 220 or 222 sealed between the sheets. It is important that the controlling element is bonded securely and inseparably to the placard.

Both language placards 200, 201 also include a securing mechanism 230 for removably securing the language placard 200, 201 to the underlying AED 10. Preferred securing mechanisms are clips, snaps, or slots. Hook and loop material or even a removable adhesive may alternatively be used.

The particular securing mechanism 230 shown in FIGS. 2a and 2b are holes for receiving a ring binding clip affixed to the AED 10. As will be described below, this embodiment allows the language placard to be flipped away from the AED to remove the placard's controlling element from its corresponding sensing element and also to uncover a second language placard with a second controlling element still in correspondence with a second sensing element. The flipped away configuration in turn enables the AED controller to switch to the second language operation.

Figure 3A:
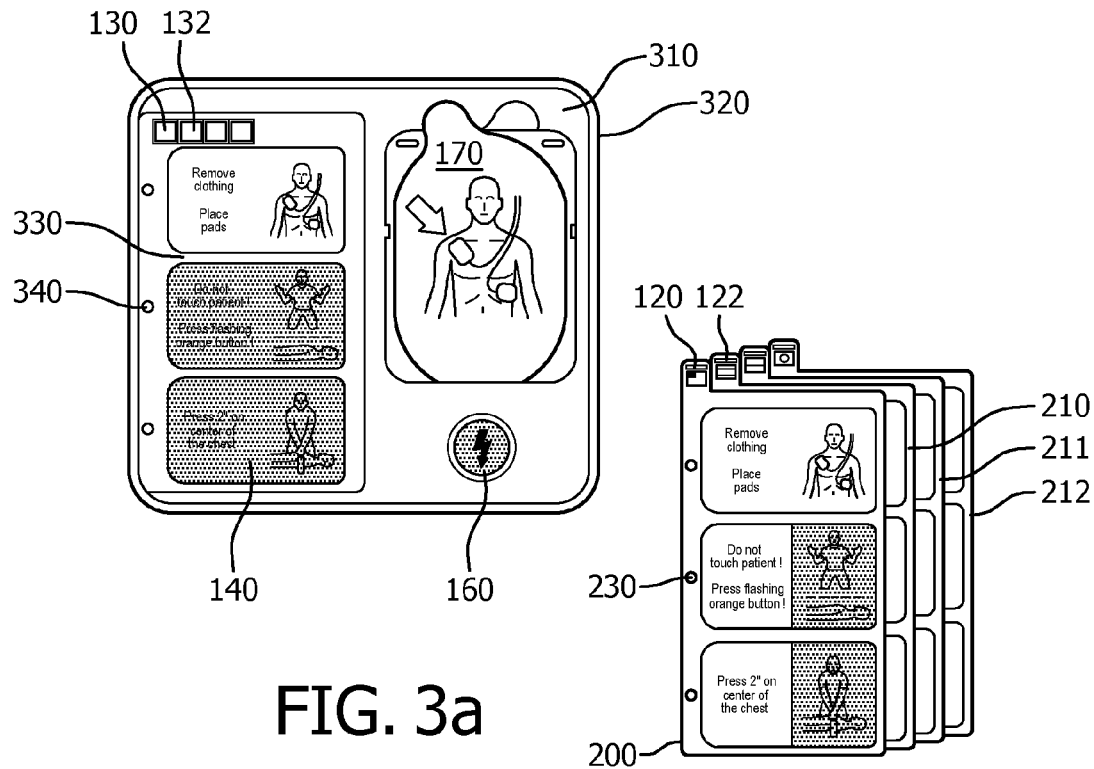
FIG. 3a and FIG. 3b illustrate an AED and a full-panel language placard according to one embodiment of the present invention, showing the components both separated and assembled.

FIG. 3a illustrates, a portable medical device, shown as an AED 310, with a language placard 200. AED 310 includes a case 320 which houses the internal components. Electrodes 170 are shown as stored with the AED 310 to allow rapid deployment during use.

A placard mount 330 on AED case 320 includes at least a highly visible region on the face of case 320 for user viewing of rescue-related instructions. Mount 330 also includes one or more sensing elements, such as 130 and 132, which is in electrical communication with the internal controller circuitry. Mount 330 is shaped to receive one or more language placards.

Optionally, case 320 includes a placard retainer 340 for holding a language placard securely in mount 330. Also, mount 330 may include one or more backlight panels 140, which the internal AED controller illuminate(s) based on a detected rescue stage or device activation. Optionally, graphic instructions may be placed directly on the mount 330. If the AED 310 is configured with a default language, written instructions in the default language may be placed directly on mount 330 as well. This option allows the AED 310 to be used even if no language placard at all is present.

FIG. 3a shows additional language placards 210, 211, 212 stacked with language placard 200, each having a controlling element tab such as second controlling element 122. Each placard may also have translucent regions underlying the respective graphic and written instructions and disposed to overlie backlight 140. Each controlling element tab is disposed to overlie a corresponding sensing element area on AED 310 when installed. A securing mechanism 230 is shown on placard 200 for securing the placard to the placard retainer 340.

Figure 3B:
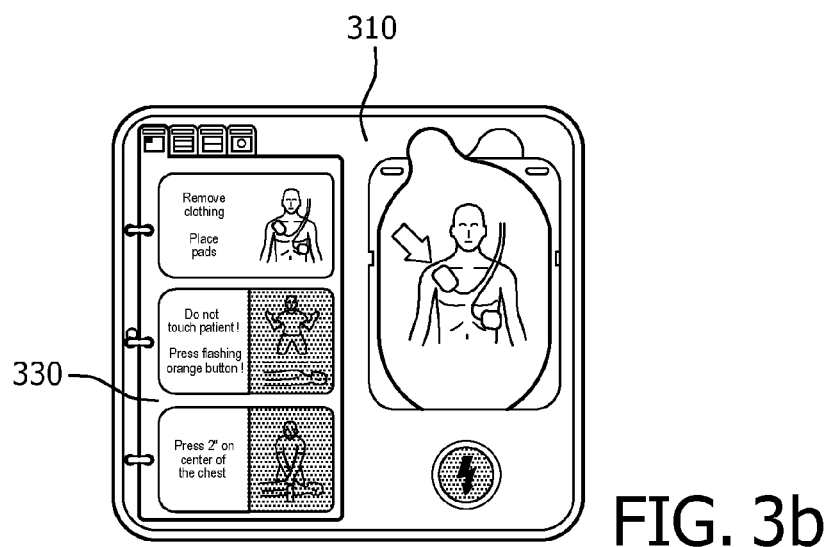

FIG. 3b illustrates the AED 310 and language placards 200, 210, 211, and 212 in an assembled state, wherein AED 310 is configured to provide user instruction prompts in the language of the top language placard 200. Although shown with multiple placards, it is within the scope of the invention to mount only a single language placard on AED 310. As is shown, the mounted and visible language placard is disposed to obscure any underlying placards and any instructions placed on the mount.

In use, the AED 310 of FIG. 3b is activated by an on/off button or similar means, not shown, whereupon AED 310 begins to guide the user with aural prompts in the first language of the visible language placard 200. AED 310 is configured, either at activation or when the language placard 200 was installed, to operate in the first language based upon the sensed presence of one or more controlling elements on the installed language placard(s). In this instance, the controlling element 120 of English language placard 200 is sensed by corresponding sensing element 130 on AED 310, so that any other sensed controlling elements are ignored. Variations of the sensed presence are of course within the scope of the invention, and extend to coded controlling element signals, combinations of controlling elements as present, or permutations of controlling elements. If no language placard is detected by the AED 310, AED 310 will begin operation in a default language.

If, during operation, the user desires to switch languages, she may do so simply by removing the language placard that is in use, and replacing it with another placard having a different language. The AED 310 will then continue the operation from that time in the different language. Thus, the invention avoids undue delay or confusion which would otherwise arise by re-starting the operation in the different language.

Figure 4:
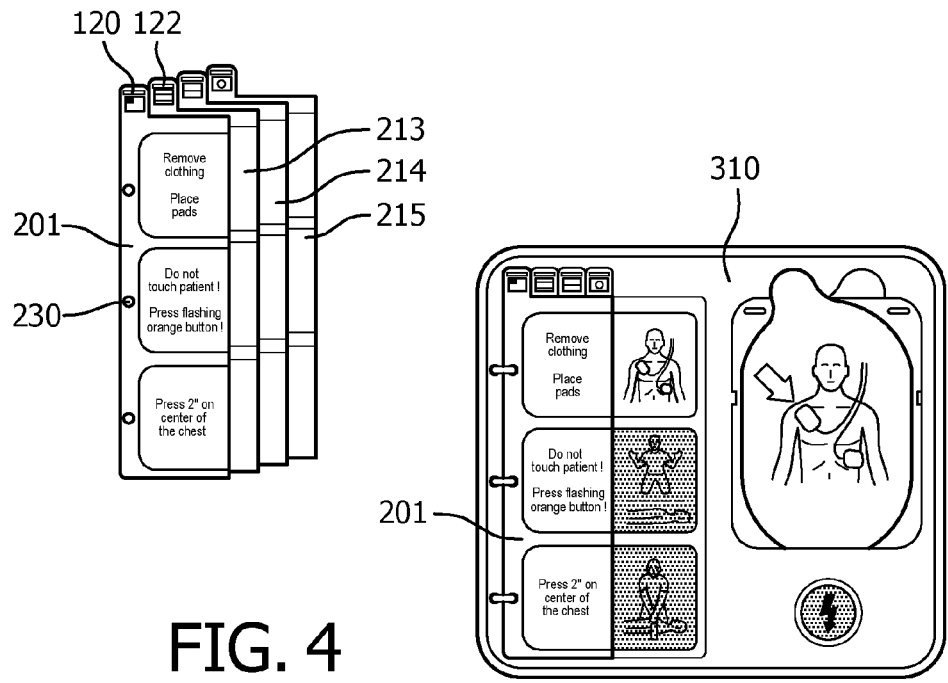
FIG. 4 illustrates an AED and a half-panel language placard according to an alternative preferred embodiment of the present invention, showing the components separate and assembled.

Now turning to FIG. 4, a variation of the invention as shown in FIG. 3 substitutes a half-panel language placard 201 for the full-panel language placard 200. In the FIG. 4 embodiment, universal graphic instructions are placed directly on the AED 310 mount. If the AED 310 is configured with a default language, written instructions in the default language may be placed directly on mount 330 as well. This option allows the AED 310 to be used even if no language placard at all is present.

FIG. 4 also shows additional half-panel language placards 213, 214, 215 stacked with half-panel language placard 210, each having a controlling element tab such as second controlling element 122. Each placard may also have translucent regions underlying the respective written instructions and disposed to overlie backlight 140. Each controlling element tab is disposed to overlie a corresponding sensing element area on AED 310 when installed. A securing mechanism 230 is shown on placard 201 for securing the placard to the placard retainer 340.

FIG. 4 also illustrates the AED 310 and language placards 201, 213, 214, and 215 in an assembled state, wherein AED 310 is configured to provide user instruction prompts in the language of the visible top language placard 201. Although shown with multiple placards, it is within the scope of the invention to mount only a single language placard on AED 310. The FIG. 4 embodiment shows how the universal graphic user instruction which is disposed directly on the AED 310 is displayed adjacent to the corresponding written instructions appearing on the half-panel language placard 201. In all other aspects, use of the AED 310 in the FIG. 4 embodiment is the same as described in the FIG. 3 embodiment.

Figure 5:
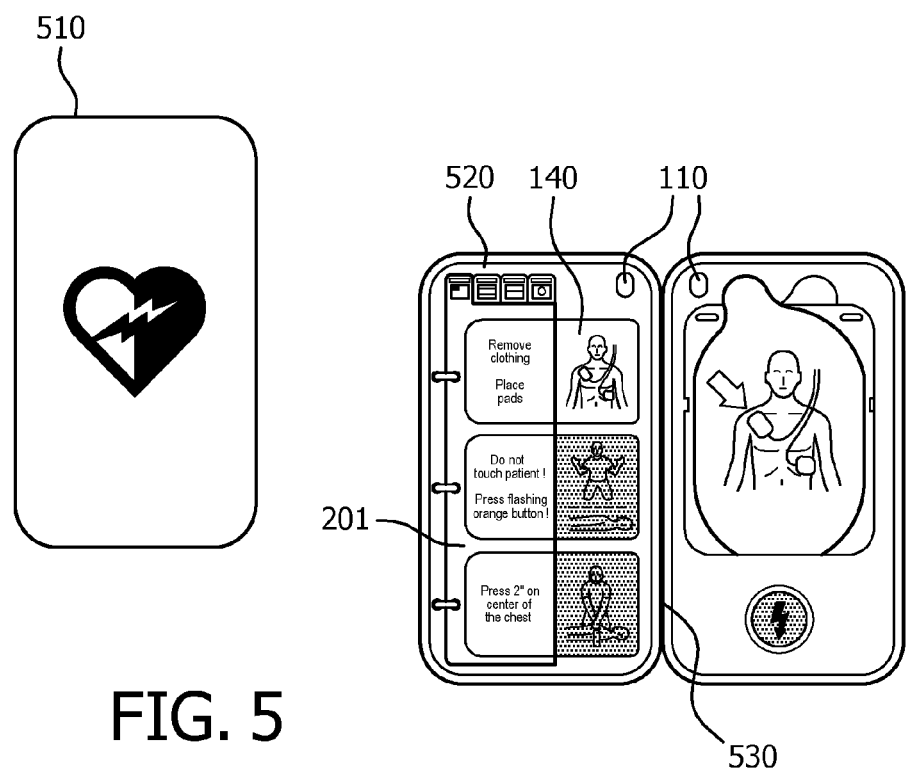
FIG. 5 illustrates a hinged-to-open AED with a language placard installed inside according to an alternative embodiment of the present invention.

FIG. 5 illustrates another embodiment of the invention, comprising a hinged-to-open AED 510 having a mount with a language placard 201 installed inside a hinged lid 520. According to this alternative embodiment of the present invention, AED 520 comprises a base unit which is joined to the hinged lid 520 by an AED case hinge 530. Power and communications are shared between the base unit and the hinged lid 520 via paths not shown.

FIG. 5 further illustrates the disposition of the case opening sensor 110, which in this embodiment is a Hall Effect sensor which generates a signal to the controller 108 when the lid 520 is opened. In use, the AED 510 may be activated by the controller when the lid is sensed open. If the controller 108 has not already configured the language according to the installed language placard 201, it does so at activation. Then, the AED 510 issues audible user prompts according to the language of the installed placard. In addition, AED 510 may further energize the backlight 140 upon activation. If the backlight 140 panel consists of several sub-panels, AED 510 may selectively energize the sub-panels of backlight 140 according to a sensed stage of the rescue. In other aspects, operation of AED 510 is similar to that described in other embodiments.

FIGS. 6a and 6b are top views of a language placard assembly 600 according to another embodiment of the present invention, wherein a first language placard 601 is hingeably attached to a second language placard 602 in a notebook-type fashion. The illustrated embodiment shows half-panel language placards 601 and 602 with similar features as previously describe placard 201. In this embodiment, two or more half-language placards identifying different languages are assembled at one edge with a language placard assembly hinge 630. Assembly hinge 630 may optionally be integrated into a securing mechanism such as securing mechanism 230 to mount the assembly of language cards onto the AED placard mount.

As can be seen in FIG. 6b, the assembly 600 can be flipped open until the desired language placard is in view. In addition, the flipping away of the language placard, such as placard 601, displaces its controlling element away from its normal position. The utility of this feature is shown in the following FIG. 7.

FIG. 7 illustrates in the top view an AED with the FIG. 6 language placard assembly 600 as installed in an AED 710. In this disposition, the AED initially senses the first language placard 601 in visible position and begins operation in the first language upon activation. As previously described, the initial configuration may be accomplished either at activation or at an earlier time when the language placard assembly 600 was mounted in the AED 710. The operation of the AED 710 continues as previously described.

If, during operation, the user desires to switch languages, she may do so using the AED 710 and language placard assembly 600. The bottom view of FIG. 7 illustrates the FIG. 7 embodiment after the user has flipped open the language placard assembly 600 to view the instructions in a second language. In this position, AED 710 senses that second language placard 602 is visible by the removal of controlling element 620 from sensing element 730. AED 710 accordingly switches language operation to the second language and continues the operation from the switched time. Thus, the invention avoids undue delay or confusion which would otherwise arise by re-starting the operation in the different language.

Variations to the aforedescribed apparatus and method are considered to fall within the scope of the claimed invention. For example, the particular arrangement of the placard with respect to the portable medical device, the content of the visual instructions, and the relative placement of the controlling elements and sensing elements may be modified within the scope of the invention.

| Table of Elements | |
|---|---|
| Element | Name |
| 10 | Automated external defibrillator (AED) |
| 20 | Language placard |
| 21 | Second language placard |
| 102 | Main Processing Unit |
| 104 | Gate Array |
| 108 | Controller |
| 110 | Case opening sensor |
| 114 | Memory |
| 120 | Controlling element |

-continued

Table of Elements

| Element | Name |
|---|---|
| 122 | Second controlling element |
| 128 | status interface |
| 130 | Sensing element |
| 132 | Second sensing element |
| 136 | on/off switch |
| 134 | battery |
| 138 | Energy source |
| 140 | Backlight panel |
| 150 | Speaker |
| 160 | shock button |
| 170 | electrodes |
| 200 | full-panel language placard |
| 201 | half-panel language placard |
| 220 | Controlling element |
| 222 | Second controlling element |
| 224 | Graphic instruction |
| 226 | Written instruction |
| 228 | Instruction panel |
| 229 | Written instruction panel |
| 230 | Securing mechanism |
| 310 | AED |
| 320 | AED case |
| 330 | Placard mount |
| 340 | Placard retainer |
| 210 | Second language placard |
| 211 | Third language placard |
| 212 | Fourth language placard |
| 213 | Second half-panel language placard |
| 214 | Third half-panel language placard |
| 215 | Fourth half-panel language placard |
| 510 | Hinged-to-open AED |
| 520 | Hinged lid |
| 530 | AED case hinge |
| 630 | Language placard assembly hinge |
| 600 | Language placard assembly |
| 620 | Controlling element |
| 601 | first language placard |
| 602 | second language placard |
| 710 | Hinged-to-open AED |
| 730 | Sensing element |

The invention claimed is:

1. A portable medical device configurable to operate in multiple languages comprising:
a controller;
a memory disposed in electrical communication with the controller, the memory comprising data relating to user instructions in a plurality of languages;
a case which houses the controller and memory and comprises a mount for a placard;
a sensing element disposed adjacent the mount and in electrical communication with the controller;
a placard having a visible user instruction in a first language and disposed to be removably secured in the mount;
a controlling element disposed on the placard such that the sensing element senses the controlling element when the placard is secured in the mount,
wherein the controller configures the portable medical device to operate in one of the plurality of languages based on the sensed controlling element.

2. The portable medical device of claim 1, wherein the portable medical device comprises an automated external defibrillator.

3. The portable medical device of claim 1, wherein the placard is translucent, and further comprising:
a backlight panel disposed under the mount, wherein the controller illuminates the user instruction through the placard during use.

4. The portable medical device of claim 3 wherein the placard comprises a plurality of panels each of which illustrate a step in the use, and further wherein the backlight panel comprises a plurality of backlights each of which underlies one of the plurality of panels, and further wherein the controller illuminates one of the plurality of backlights in accordance with a sensed progress of the use.

5. The portable medical device of claim 1 further comprising a default language user instruction disposed on the mount such that the default language user instruction is obscured when the placard is removably secured in the mount.

6. The portable medical device of claim 1, further comprising a universal graphic user instruction disposed to be visible to the user at all times during use.

7. The portable medical device of claim 1, wherein the case further comprises a hinged lid in which the placard and mount are disposed on an inner surface of the lid.

8. The portable medical device of claim 7, wherein the placard is translucent, and further comprising:
a backlight panel disposed under the mount,
wherein the controller is further disposed to sense the opening of the lid and illuminates the user instruction through the placard based on the sensed opening.

9. The portable medical device of claim 1, wherein the sensing element and controlling element are selected from one of the group of optical, radio frequency identification (RFID), electrical, hall effect or mechanical contact elements.

10. The portable medical device of claim 1, wherein the controller is disposed to switch from one language to a second language in the plurality of languages based on a placement or removal of the placard during use, and continue the use in the second language.

11. The portable medical device of claim 1 further comprising:
a second sensing element in electrical communication with the controller;
a second placard having a visible user instruction in a second language and disposed to be removably secured in the mount;
a second controlling element disposed on the second placard such that the second sensing element senses the second controlling element when the second placard is secured in the mount,
wherein the controller configures the portable medical device to operate in the second language based on the second sensed controlling element.

12. A placard for an automated external defibrillator, comprising:
a panel having a written instruction in a first language;
a controlling element having a unique identifier of the first language; and
a securing element for mounting the placard onto the automated external defibrillator.

13. The placard of claim 12, further comprising:
a second panel having a written instruction in a second language;
a second controlling element having a unique identifier of the second language; and
a hinge for hingeably attaching the second panel to the panel.

14. The placard of claim 13, wherein the hinge is integral with the securing element.

15. The placard of claim 12, wherein the panel is translucent.

16. The placard of claim 12, wherein the written instructions are disposed on the panel such that when the placard is mounted, the written instructions lie adjacent to universal graphic instructions disposed on the automated external defibrillator.

17. The placard of claim 12, wherein the controlling element is selected from one of the group comprising an optical element, electrical contact, radio frequency identification element, hall effect or mechanical operator.

18. A method for operating an automated external defibrillator in a plurality of languages, the method comprising the steps of
providing an automated external defibrillator having a plurality of languages for audible user instructions stored in memory and a sensing element for selecting one of the plurality of languages;
mounting a placard having written instructions in a first language and a controlling element onto the automated external defibrillator; and
automatically selecting the first language for the automated external defibrillator based on the mounting step.

19. The method of claim 18, wherein the step of mounting further comprises hingeably mounting the placard onto the automated external defibrillator, and further comprising the steps of:
operating the automated external defibrillator in the first language;
flipping the placard away from the automated external defibrillator about the hingable mount; and
automatically switching to a second language in the plurality of languages based on the flipping step.

20. The method of claim 19, wherein the step of automatically switching occurs during use, and wherein the audible user instructions continue in the second language.

* * * * *